United States Patent
Iwasa et al.

(10) Patent No.: US 11,206,848 B2
(45) Date of Patent: Dec. 28, 2021

(54) COFFEE BEANS WITH HIGH FATTY ACID METHYL ESTER CONTENT AND METHOD OF MAKING SAME

(71) Applicant: SUNTORY HOLDINGS LIMITED, Osaka (JP)

(72) Inventors: Keiko Iwasa, Kyoto (JP); Koichi Nakahara, Kyoto (JP); Harumichi Seta, Kyoto (JP)

(73) Assignee: SUNTORY HOLDINGS LIMITED, Osaka (JP)

( * ) Notice: Subject to any disclaimer, the term of this patent is extended or adjusted under 35 U.S.C. 154(b) by 335 days.

(21) Appl. No.: 16/327,075

(22) PCT Filed: Aug. 21, 2017

(86) PCT No.: PCT/JP2017/029767
§ 371 (c)(1),
(2) Date: Feb. 21, 2019

(87) PCT Pub. No.: WO2018/038047
PCT Pub. Date: Mar. 1, 2018

(65) Prior Publication Data
US 2019/0223463 A1 Jul. 25, 2019

(30) Foreign Application Priority Data
Aug. 22, 2016 (JP) .............................. JP2016-162151

(51) Int. Cl.
*A23F 5/02* (2006.01)
*A23F 5/04* (2006.01)
*A23F 5/24* (2006.01)
*G01N 33/02* (2006.01)

(52) U.S. Cl.
CPC .................. *A23F 5/02* (2013.01); *A23F 5/04* (2013.01); *A23F 5/24* (2013.01); *G01N 33/02* (2013.01)

(58) Field of Classification Search
CPC ..... A23F 5/02; A23F 5/04; A23F 5/24; G01N 33/02
See application file for complete search history.

(56) References Cited

U.S. PATENT DOCUMENTS

| | | | |
|---|---|---|---|
| 4,820,537 A | 4/1989 | Katz | |
| 6,586,658 B1 * | 7/2003 | Peoples .................. | C12N 15/52 435/468 |
| 2004/0081724 A1 | 4/2004 | Dria et al. | |

(Continued)

FOREIGN PATENT DOCUMENTS

| | | |
|---|---|---|
| EP | 0331852 A2 | 9/1989 |
| EP | 1555885 A2 | 7/2005 |

(Continued)

OTHER PUBLICATIONS

Oliveira et al. 2006. LWT. vol. 39. pp. 235-239.*

(Continued)

*Primary Examiner* — Anthony J Weier
(74) *Attorney, Agent, or Firm* — Faegre Drinker Biddle & Reath LLP

(57) ABSTRACT

Coffee beans having an increased flavor component, a method for increasing a flavor component in coffee beans, and a method for evaluating coffee beans are provided. A fatty acid methyl ester content of coffee beans is increased.

12 Claims, 4 Drawing Sheets

(56) References Cited

U.S. PATENT DOCUMENTS

| | | |
|---|---|---|
| 2007/0190207 A1 | 8/2007 | Takahashi et al. |
| 2009/0130259 A1 | 5/2009 | Yomo et al. |
| 2011/0250339 A1 | 10/2011 | Onishi et al. |
| 2013/0156928 A1 | 6/2013 | Bytof et al. |

FOREIGN PATENT DOCUMENTS

| | | |
|---|---|---|
| EP | 1695631 A1 | 8/2006 |
| EP | 1875807 A1 | 1/2008 |
| EP | 2382868 A1 | 11/2011 |
| JP | H01-309640 A | 12/1989 |
| JP | 2006-503592 A | 2/2006 |
| JP | 2013-524821 A | 6/2013 |
| JP | 2014-11984 A | 1/2014 |
| WO | WO-2004/037007 A2 | 5/2004 |
| WO | WO-2005/029969 A1 | 4/2005 |
| WO | WO-2005/072535 A1 | 8/2005 |
| WO | WO-2006/101196 A1 | 9/2006 |
| WO | WO-2010/038867 A1 | 4/2010 |
| WO | WO-2016/066167 A1 | 5/2016 |

OTHER PUBLICATIONS

Lee et al. Food Chemistry. May 2016. vol. 211. pp. 925-936.*
Braham et al. Coffee Pulp. 1979. pp. 11-16.*
Flament. Coffee Flavor Chemistry. 2001. pp. 171 and 172.*
European Patent Office, Extended European Search Report for EP Patent Application No. 17843527.7, dated Apr. 7, 2020.
Jham, Gulab N., et al., "The Use of Fatty Acid Profile as a Potential Marker for Brazilian Coffee (*Coffee arabica* L.) for Corn Adulteration," J. Braz. Chem. Soc., vol. 19, No. 8, 2008, pp. 1462-1467.
Internatinal Search Report dated Nov. 14, 2017 for PCT/JP2017/029767.

* cited by examiner

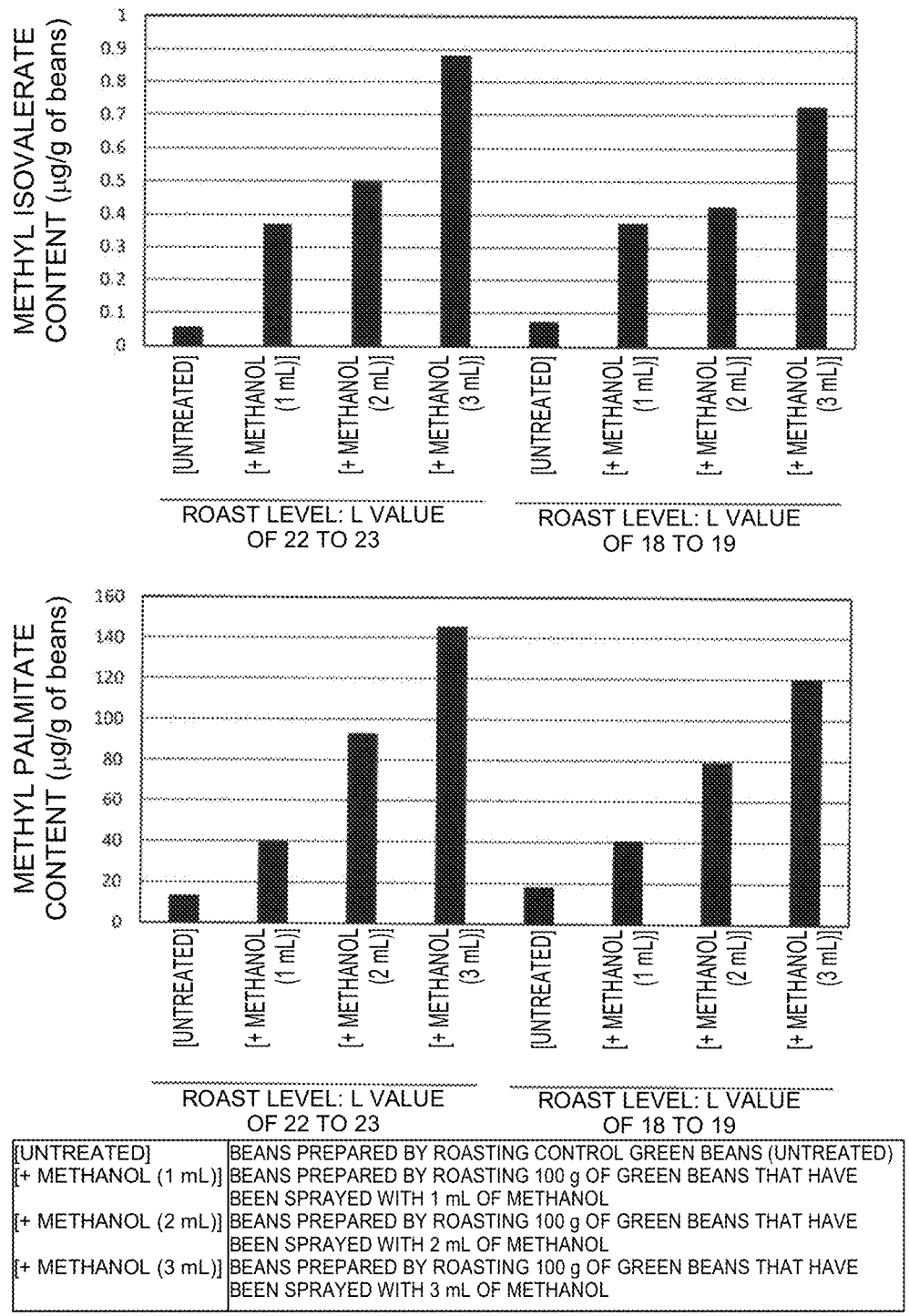

Fig. 2

FATTY ACID METHYL ESTER CONTENT OF ROASTED BEANS (METHYL ISOVALERATE CONTENT AND METHYL PALMITATE CONTENT)

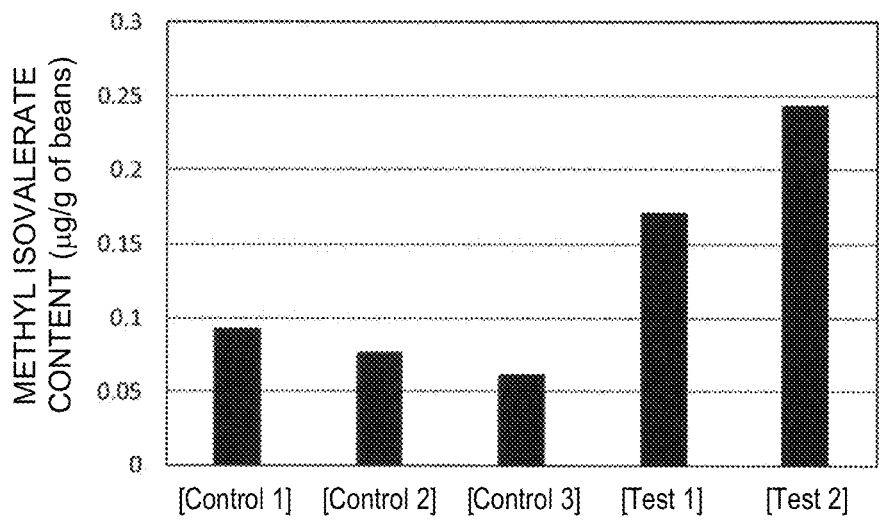

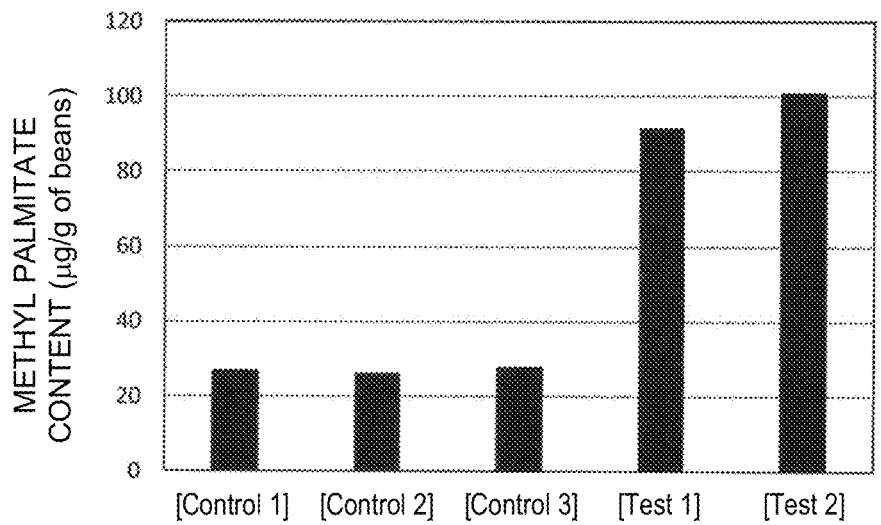

| [Control 1] | BEANS PREPARED BY ROASTING CONTROL GREEN BEANS (UNTREATED) |
| [Control 2] | BEANS PREPARED BY ROASTING GREEN BEANS TREATED IN 25 mL OF WATER |
| [Control 3] | BEANS PREPARED BY ROASTING GREEN BEANS INCUBATED IN 25 mL OF WATER AT 45°C FOR 48 HOURS |
| [Test 1] | BEANS PREPARED BY ROASTING GREEN BEANS INCUBATED AT 45°C FOR 48 HOURS UNDER CONDITIONS OF ADDITION OF COFFEE PULP AND PERICARP, 1 mL OF PECTINASE PL, AND 24 mL OF WATER |
| [Test 2] | BEANS PREPARED BY ROASTING GREEN BEANS INCUBATED AT 45°C FOR 48 HOURS UNDER CONDITIONS OF ADDITION OF COFFEE PULP AND PERICARP AND 25 mL OF WATER |

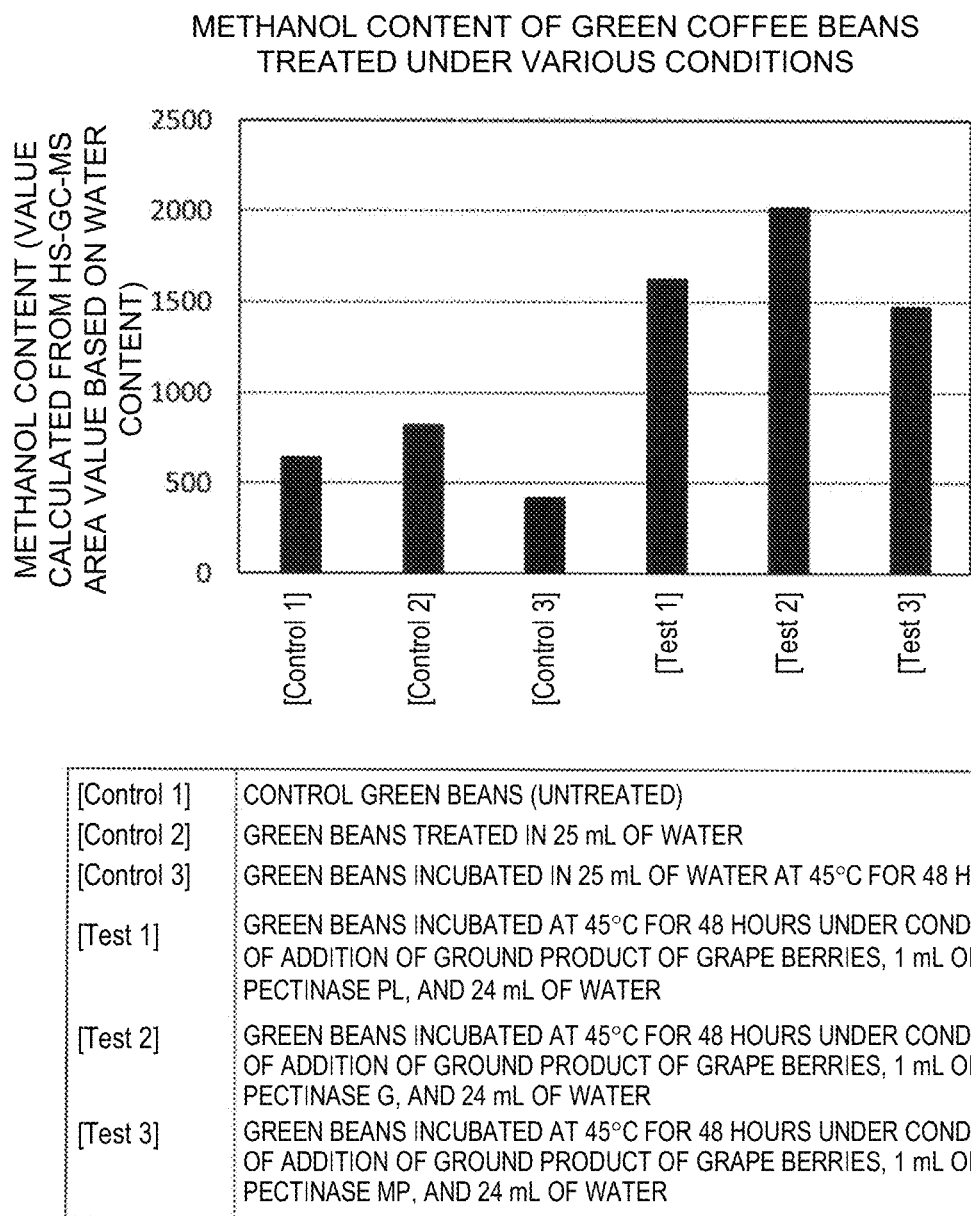

COMPARISON BETWEEN ACIDITY AND BITTERNESS INTENSITY OF COFFEE BEVERAGE 1 (SHOWN AS 1) AND COFFEE BEVERAGE 3 (SHOWN AS 3) (COLLECTED ANSWERS OF PANELISTS GIVING CORRECT ANSWERS IN TRIANGLE DISCRIMINATION TEST)

RELATIVE RELATIONSHIP BETWEEN ACIDITY AND BITTERNESS INTENSITY OF COFFEE BEVERAGES 1 TO 3 (X = COFFEE BEVERAGE 1; X+A = COFFEE BEVERAGE 2; Z = COFFEE BEVERAGE 3)

COFFEE BEANS WITH HIGH FATTY ACID METHYL ESTER CONTENT AND METHOD OF MAKING SAME

CROSS REFERENCES TO RELATED APPLICATIONS

This application is the National Stage of International Application No. PCT/JP2017/029767 filed Aug. 21, 2017, and claims benefit of Japanese Application No. 2016-162151 filed on Aug. 22, 2016.

TECHNICAL FIELD

The present invention relates to coffee beans and the like. The present invention particularly relates to coffee beans having a fatty acid methyl ester content of a specific value or more, a method for increasing fatty acid methyl ester in coffee beans, and a method for evaluating coffee beans.

BACKGROUND ART

Coffee beans are a general term for seeds (coffee seeds) obtained by a step (a refining step) of removing pulp and thin skin from fruits of a plant belonging to the family Rubiaceae (referred to as a coffee fruit or a coffee cherry) called *Coffea arabica* and for beans prepared by processing such seeds. In the above coffee beans, coffee beans before a roasting step in which coffee beans are roasted by heat are referred to as green coffee beans, and coffee beans after the roasting step are referred to as roasted coffee beans. The roasted coffee beans are ground and coffee is extracted by filtration from the ground beans with an undiluted extracting solution such as boiling water and water using a filter such as a filter cloth and a mesh. Accordingly, a coffee beverage is produced.

Coffee beverages have been universally loved by consumers as their luxury beverages, and a demand for the coffee beverages is growing and growing and consumer needs are also becoming diversified. However, a flavor of coffee beverages varies significantly depending on various conditions such as species of coffee beans, growing land, and growing conditions. For that reason, there has been a demand for an objective indicator to pre-evaluate coffee beans suitable for producing coffee beverages having a flavor that meets the consumer needs (PTL 1).

CITATION LIST

Patent Literature

PTL 1: Japanese Patent Application Publication No. 2014-011984

SUMMARY OF INVENTION

Technical Problem

An object of the present invention is to determine a component in coffee beans that highly contributes to the flavor of coffee and to provide coffee beans containing such a component in high concentrations.

Solution to Problem

The present inventors repeatedly made an intensive study to achieve the above object, and consequently found that fatty acid methyl ester contained in coffee beans highly contributes to a flavor of coffee. Further, the present inventors found that adding a methyl group donor as a fatty acid methyl ester precursor to coffee beans and heating the resulting coffee beans increase a fatty acid methyl ester content of coffee beans. The present invention was completed based on the above findings.

That is, the present invention relates to the following matters. However, the present invention is not limited to these matters.

(1) A coffee bean having a fatty acid methyl ester content of 29.5 µg or more per gram of the coffee bean.
(2) The coffee bean according to (1), wherein fatty acid methyl ester comprises at least one of methyl isovalerate and methyl palmitate.
(3) The coffee bean according to (2), wherein a methyl isovalerate content is 0.10 µg or more per gram of the coffee bean.
(4) The coffee bean according to (2), wherein a methyl palmitate content is 28.0 µg or more per gram of the coffee bean.
(5) The coffee bean according to any of (1) to (4), wherein the coffee bean is a roasted coffee bean.
(6) The coffee bean according to any of (1) to (5), wherein an L value is 14 or more.
(7) A coffee beverage prepared by using the coffee bean according to any of (1) to (6).
(8) A coffee beverage having a methyl isovalerate content of 25 ppb or more.
(9) A method for increasing a fatty acid methyl ester content of a coffee bean, comprising a step a) of supplying a methyl group donor to a coffee bean.
(10) The method according to (9) further comprising a step b) of warm-treating or normal temperature-treating the coffee bean.
(11) The method according to (9) or (10), further comprising a step c) of roasting the coffee bean.
(12) The method according to any of (9) to (11), wherein the fatty acid methyl ester content of the coffee bean is 29.5 µg or more per gram of the coffee bean.
(13) The method according to any of (9) to (12), wherein the methyl group donor comprises at least one or more selected from the group consisting of methanol, a pectic ingredient, trigonelline, and S-methylmethionine.
(14) The method according to (13), wherein the pectic ingredient comprises at least one or more of pectin and a pectin-containing material.
(15) The method according to (14), wherein the pectin-containing material comprises pulp of a plant.
(16) The method according to (15), wherein the pulp of a plant comprises at least one of coffee pulp and a grape berry.
(17) The method according to any of (9) to (16), further comprising a step of supplying pectinase in step a).
(18) A method for evaluating a coffee bean having a good flavor, comprising:
 a step of measuring a fatty acid methyl ester content of a coffee bean; and
 a step of comparing the fatty acid methyl ester content with a predetermined value.
(19) The method according to (18), wherein the predetermined value of the fatty acid methyl ester content is 29.5 µg or more per gram of the coffee bean, and
 a coffee bean determined to have a fatty acid methyl ester content of 29.5 µg or more per gram of the coffee bean is evaluated as having a good flavor.
(20) The method according to (18) or (19), wherein the fatty acid methyl ester comprises at least one of methyl isovalerate and methyl palmitate.

Advantageous Effects of Invention

In the present invention, coffee beans having an increased content of fatty acid methyl ester that contributes to the flavor of coffee can be provided. Further, according to the present invention, the flavor of coffee can be made stronger and the flavor of coffee beans can be evaluated based on fatty acid methyl ester as an indicator.

BRIEF DESCRIPTION OF DRAWINGS

FIG. 1 shows a methyl isovalerate content (μg/g of beans) and a methyl palmitate content (μg/g of beans) in roasted coffee beans prepared by roasting green coffee beans sprayed with methanol.

FIG. 2 shows a methyl isovalerate content (μg/g of beans) and a methyl palmitate content (μ/g of beans) in roasted coffee beans prepared by roasting green coffee beans supplied with coffee pulp and pericarp and further treated with adding pectinase or water.

FIG. 3 shows a methanol content of green coffee beans (a value converted from a HS-GC-MS area value based on a water content) supplied with a ground product of grape berries and further treated with pectinase or water.

DESCRIPTION OF EMBODIMENTS

Figure 4:
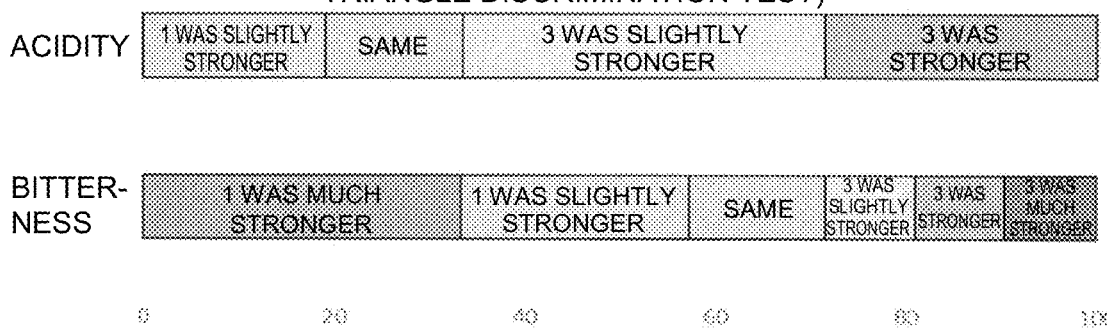
FIG. 4 shows a comparison result of perception characteristics including acidity and bitterness in a sensory evaluation test conducted, by ordinary panelists (42 working males in their twenties to forties), on a beverage produced by using roasted coffee beans of the same quality as the roasted coffee beans used for a commercially available canned coffee (Coffee beverage 1) and a beverage produced by using high-quality roasted coffee beans (Coffee beverage 3).
Figure 5:
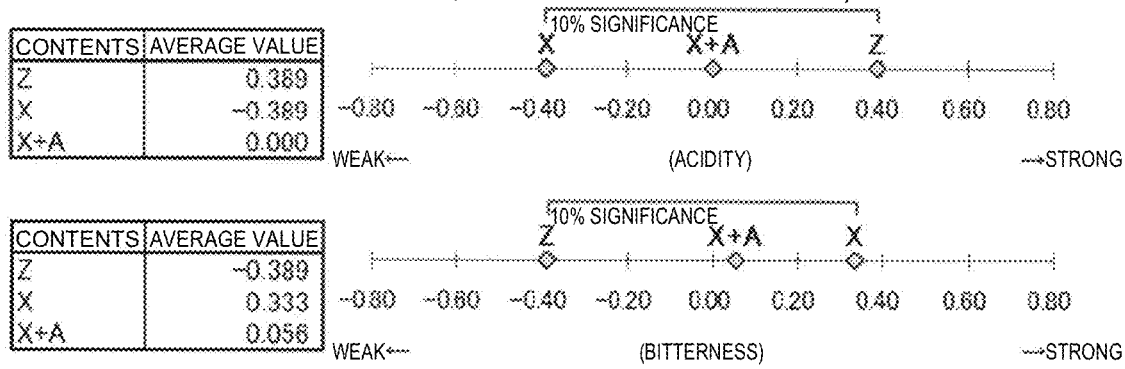
FIG. 5 shows a result of an evaluation made by professional panelists in regard to a proportional relationship of an intensity of acidity and bitterness of a beverage produced by using roasted coffee beans of the same quality as the roasted coffee beans used for a commercially available canned coffee (Coffee beverage 1: shown as "X" in FIG. 5), a beverage produced by adding methyl isovalerate to Coffee beverage 1 (Coffee beverage 2: shown as "X+A" in FIG. 5), and a beverage produced by using high-quality roasted coffee beans (Coffee beverage 3: shown as "Z" in FIG. 5) evaluated.

1. Coffee Beans 1-1. Fatty Acid Methyl Ester

In one aspect of the present invention, coffee beans having a fatty acid methyl ester content within a specific range is provided.

The plural number of fatty acid methyl esters contained in coffee beans has been known, and these fatty acid methyl esters includes the ones having a fruity and fruit-like aroma that highly contribute to a peculiar flavor of coffee. The present inventors found that a coffee beverage produced by using coffee beans having a fatty acid methyl ester content within a specific range has a good flavor. A lower limit of the fatty acid methyl ester content of the coffee beans of the present invention is 29.5 μg or more per gram of coffee beans (29.5 μg or more/g of beans), preferably 35.0 μg or more/g of beans, more preferably 40.0 μg or more/g of beans. An upper limit of the fatty acid methyl ester content of the coffee beans of the present invention is not limited to a particular value and is preferably 60000 μg or less/g of beans, more preferably 6000 μg or less/g of beans.

A kind of fatty acid methyl ester contained in the coffee beans of the present invention is not limited to a particular kind, and the fatty acid methyl ester is preferably one or more selected from the group consisting of short-chain to long-chain fatty acid methyl ester having a carbon chain of 1 to 28 carbon atoms. Preferably, the fatty acid methyl ester contained in the coffee beans of the present invention is one or more selected from the group consisting of methyl formate, methyl acetate, methyl propionate, methyl butyrate, methyl valerate, methyl isovalerate, methyl caproate, methyl caprylate, methyl caprate, methyl myristate, methyl palmitate, methyl stearate, methyl linoleate, and methyl oleate. From the viewpoint of providing a better flavor, the coffee beans of the present invention contain two or more components and more preferably contain three or more components each selected from the above fatty acid methyl esters, and further more preferably contain all the above fatty acid methyl esters. Moreover, the fatty acid methyl esters contained in the coffee beans of the present invention more preferably includes at least one of methyl isovalerate and methyl palmitate.

The coffee beans of the present invention contain various kinds of flavor components other than the fatty acid methyl esters. The flavor components other than the fatty acid methyl esters contained in the coffee beans of the present invention are not limited to particular components. However, examples of the flavor components include furfuryl methyl ether and methyl 2-furancarboxylate.

A content of each of the components including methyl formate, methyl acetate, methyl propionate, methyl butyrate, methyl valerate, methyl isovalerate, methyl caproate, methyl caprylate, methyl caprate, methyl myristate, methyl palmitate, methyl stearate, methyl linoleate, and methyl oleate in the coffee beans of the present invention is not limited to a particular content and is preferably 29.5 μg or more per gram of coffee beans (29.5 μg or more/g of beans), more preferably 35.0 μg or more/g of beans, further more preferably 40.0 μg or more/g of beans, and it is preferably 60000 μg or less/g of beans, more preferably 6000 μg or less/g of beans. Further, a methyl isovalerate content of the coffee beans of the present invention is preferably 0.10 μg or more/g of beans, more preferably 0.12 μg or more/g of beans, further more preferably 0.14 μg or more/g of beans, particularly preferably 0.17 μg or more/g of beans, and it is preferably 80 μg or less/g of beans, more preferably 8 μg or less/g of beans. Moreover, a methyl palmitate content of the coffee beans of the present invention is preferably 28.0 m or more/g of beans, more preferably 34.0 μg or more/g of beans, further more preferably 38.0 μg or more/g of beans, and it is preferably 40000 μg or less/g of beans, more preferably 4000 μg or less/g of beans.

Fatty acid methyl ester can be measured by a publicly known method, and such a method includes, for example, LC-MS method, GC-MS method, LC method, GC method, and spectrometry such as a near infrared spectrum.

1-2. Coffee Beans, Green Coffee Beans, and Roasted Coffee Beans

A production place and a species of the coffee beans of the present invention are not limited to a particular production place and a particular species. Examples of the production place of the coffee beans include Brazil, Colombia, Tanzania, Mocha, Kilimanjaro, Mandheling, and Blue Mountain, and examples of the species of the coffee beans include *arabica, robusta,* and *liberica*. Coffee beans from one production place or coffee beans of one species may be used, or a combination of coffee beans from different production places or coffee beans of different species may be used.

In the present specification, "green coffee beans" refers to coffee beans before a roasting step that is a process in which the coffee beans are roasted by heat, and "roasted coffee beans" refers to coffee beans after the roasting step. The coffee beans of the present invention may be either green coffee beans or roasted coffee beans and are not limited to these in particular.

It is generally considered that fatty acid methyl ester in coffee beans tends to increase by heat. However, according to the present invention, it is possible to include a specific fatty acid methyl ester in an amount that sufficiently contributes to a flavor in the coffee beans even by a low level of heat. An L value of the coffee beans of the present invention is not limited to a particular value and is preferably 14 or more, more preferably 18 or more, further more preferably 22 or more, further more preferably 28 or more.

When the coffee beans of the present invention are roasted coffee beans, a lower limit of a fatty acid methyl ester content is 29.5 µg or more per gram of roasted coffee beans (29.5 µg or more/g of beans), preferably 35.0 µg or more/g of beans, more preferably 40.0 µg or more/g of beans. When the coffee beans of the present invention are roasted coffee beans, an upper limit of the fatty acid methyl ester content is not limited to a particular value and is preferably 60000 µg or less/g of beans, more preferably 6000 µg or less/g of beans.

When the coffee beans of the present invention are roasted coffee beans, a content of each of the components including methyl formate, methyl acetate, methyl propionate, methyl butyrate, methyl valerate, methyl isovalerate, methyl caproate, methyl caprylate, methyl caprate, methyl myristate, methyl palmitate, methyl stearate, methyl linoleate, and methyl oleate is not limited to a particular content, and is preferably 29.5 µg or more per gram of roasted coffee beans (29.5 µg or more/g of beans), more preferably 35.0 µg or more/g of beans, further more preferably 40.0 µg or more/g of beans, and it is preferably 60000 µg or less/g of beans, more preferably 6000 µg or less/g of beans. When the coffee beans of the present invention are roasted coffee beans, a methyl isovalerate content is preferably 0.10 µg or more/g of beans, more preferably 0.12 µg or more/g of beans, further more preferably 0.15 µg or more/g of beans, particularly preferably 0.17 µg or more/g of beans, and it is preferably 80 µg or less/g of beans, more preferably 8 µg or less/g of beans. Further, when the coffee beans of the present invention are roasted coffee beans, a methyl palmitate content is preferably 28.0 µg or more/g of beans, more preferably 34.0 µg or more/g of beans, further more preferably 38.0 µg or more/g of beans, and it is preferably 40000 µg or less/g of beans, more preferably 4000 µg or less/g of beans.

In the present invention, a roast level of roasted coffee beans is determined based on an L value measured with a color-difference meter as an indicator, and the coffee beans may be roasted so that the L value of the roasted coffee beans is preferably 14 or more, more preferably 14 to 30, further more preferably 16 to 26. The roast level is measured with a spectrocolorimeter by putting ground beans into a cell of the spectrocolorimeter and sufficiently tapping the cell. As the spectrocolorimeter, SE-2000 manufactured by NIPPON DENSHOKU INDUSTRIES CO., LTD. can be used.

In the present invention, a roasting method and a roasting condition are not limited to a particular method and a particular condition, and the coffee beans may be finished to a roast level (light, cinnamon, medium, high, city, full city, French, or Italian) according to a species of coffee beans and a prescribed purpose using a device equipped with a horizontal (transverse) drum, a vertical (longitudinal) drum, a vertical rotating bowl, a fluidized bed, a pressurized vessel, or the like with a heating style such as direct fire, hot air, semi-hot air, charcoal fire, far-infrared rays, microwave, superheated steam, and the like.

When the coffee beans of the present invention are green coffee beans, a lower limit of a fatty acid methyl ester content is 29.5 µg or more per gram of green coffee beans (29.5 µg or more/g of beans), preferably 35.0 µg or more/g of beans, more preferably 40.0 µg or more/g of beans. Further, when the coffee beans of the present invention are green coffee beans, an upper limit of the fatty acid methyl ester content is not limited to a particular value and is preferably 60000 µg or less/g of beans, more preferably 6000 µg or less/g of beans.

When the coffee beans of the present invention are green coffee beans, a content of each of the components including methyl formate, methyl acetate, methyl propionate, methyl butyrate, methyl valerate, methyl isovalerate, methyl caproate, methyl caprylate, methyl caprate, methyl myristate, methyl palmitate, methyl stearate, methyl linoleate, and methyl oleate is not limited to a particular content and is preferably 29.5 µg or more per gram of green coffee beans (29.5 µg or more/g of beans), more preferably 35.0 µg or more/g of beans, further more preferably 40.0 µg or more/g of beans, and it is preferably 60000 µg or less/g of beans, more preferably 6000 µg or less/g of beans. Further, when the coffee beans of the present invention are green coffee beans, a methyl isovalerate content is preferably 0.10 µg or more/g of beans, more preferably 0.12 µg or more/g of beans, further more preferably 0.14 µg or more/g of beans, particularly preferably 0.17 µg or more/g of beans, and it is preferably 80 µg or less/g of beans, more preferably 8 µg or less/g of beans. Moreover, when the coffee beans of the present invention are green coffee beans, a methyl palmitate content is preferably 28.0 µg or more/g of beans, more preferably 34.0 µg or more/g of beans, further more preferably 38.0 µg or more/g of beans, and it is preferably 40000 µg or less/g of beans, more preferably 4000 µg or less/g of beans.

1-3. Ground Beans

The present invention is not limited to a particular form of beans and may be ground beans, for example. The coffee beans can be ground by a common method such as dry grinding and wet grinding.

A lower limit of a fatty acid methyl ester content of the ground coffee beans of the present invention is 29.5 µg or more per gram of ground coffee beans (29.5 µg or more/g of beans), preferably 35.0 µg or more/g of beans, more preferably 40.0 µg or more/g of beans. Further, an upper limit of the fatty acid methyl ester content of the ground coffee beans of the present invention is not limited to a particular value and is preferably 60000 µg or less/g of beans, more preferably 6000 µg or less/g of beans. A methyl isovalerate content of the ground coffee beans of the present invention is preferably 0.10 µg or more/g of beans, more preferably 0.12 µg or more/g of beans, further more preferably 0.14 µg or more/g of beans, particularly preferably 0.17 µg or more/g of beans, and it is preferably 80 µg or less/g of beans, more preferably 80 µg or less/g of beans. Further, a methyl palmitate content of the ground coffee beans of the present invention is preferably 28.0 µg or more/g of beans, more preferably 34.0 µg or more/g of beans, further more preferably 38.0 µg or more/g of beans, and it is preferably 40000 µg or less/g of beans, more preferably 4000 µg or less/g of beans.

A species and a production place of coffee beans as a raw material for the ground coffee beans of the present invention, a roast level, a roasting method, and a kind of fatty acid methyl ester are described as in Coffee beans above.

1-4. Coffee Beverage

In another aspect of the present invention, a coffee beverage may be provided.

A fatty acid methyl ester content of the coffee beverage of the present invention is not limited to a particular content and is preferably 20 ppb or more, 24 ppb or more, 25 ppb or more, 35 ppb or more, more preferably 49 ppb or more, further more preferably 50 ppb or more, particularly preferably 90 ppb or more, and it is preferably $1.0 \times 10^6$ ppb or less, more preferably $1.0 \times 10^5$ ppb or less.

A kind of the fatty acid methyl ester contained in the coffee beverage of the present invention is not limited to a particular kind and is preferably one or more selected from the group consisting of short-chain to long-chain fatty acid methyl esters having a carbon chain of 1 to 28 carbon atoms. The fatty acid methyl ester contained in the coffee beverage of the present invention is typically one or more selected from the group consisting of methyl formate, methyl acetate, methyl propionate, methyl butyrate, methyl valerate, methyl isovalerate, methyl caproate, methyl caprylate, methyl caprate, methyl myristate, methyl palmitate, methyl stearate, methyl linoleate, and methyl oleate. A content of each of the fatty acid methyl ester components contained in the coffee beverage of the present invention is also not limited to a particular kind and is preferably 20 ppb or more, 24 ppb or more, 25 ppb or more, 35 ppb or more, more preferably 49 ppb or more, further more preferably 50 ppb or more, particularly preferably 90 ppb or more, and it is preferably $1.0 \times 10^6$ ppb or less, more preferably $1.0 \times 10^5$ ppb or less.

A lower limit of a methyl isovalerate content of the coffee beverage of the present invention is 20 ppb or more, 24 ppb or more, 25 ppb or more, 35 ppb or more, more preferably 49 ppb or more, further more preferably 50 ppb or more, particularly preferably 90 ppb or more. Further, an upper limit of a content of each component in the coffee beverage of the present invention is not limited to a particular value and is preferably $1.0 \times 10^4$ ppb or less, more preferably $1.0 \times 10^3$ ppb or less, further preferably 500 ppb or less.

The coffee beverage of the present invention may be produced by using the above-described coffee beans or ground coffee beans. The coffee beverage of the present invention is not limited to a particular beverage as long as a beverage has a peculiar flavor of coffee. Examples of such a beverage include an unsweetened or sweetened coffee beverage and a coffee beverage containing milk. If necessary, raw materials, which are usually blended in beverages, including a coloring agent and a pigment such as a caramel, an antifoaming agent, a thickener, and an emulsifier, and the like may be blended in the coffee beverage of the present invention. A species and a production place of the coffee beans as a raw material for the coffee beverage of the present invention, a roast level, and the like are described as in Coffee beans above.

The coffee beverage of the present invention may be filled into a container that can be stored (for example, plastic bottles, glass bottles and jars, cans, or paper cartons). The container preferably has a lid that can seal the container, and examples of such a container include a formed container (a PET bottle as it is called) made of polyethylene terephthalate as a main component, a bottle can made of metal such as aluminum and steel. A carbonated coffee beverage of the present invention is preferably filled into a container by an aseptic filling device. The aseptic filling device generally refers to a device configured to fill contents prepared by high-temperature short-time pasteurization into a sterile container in an aseptic environment and to seal the container.

2. Method for Increasing Fatty Acid Methyl Ester in Coffee Beans

The plural number of fatty acid methyl esters contained in coffee beans have been known, and these fatty acid methyl esters includes the ones having a fruity and fruit-like aroma that highly contribute to a peculiar flavor of coffee. The present inventors found that the fatty acid methyl ester content of coffee beans is increased by treating the coffee beans in a particular way. Hereinafter, a method for increasing fatty acid methyl ester of the present invention will be described in detail.

2-1. A Method for Increasing Fatty Acid Methyl Ester by Supplying a Methyl Group Donor In another aspect of the present invention, a method for increasing fatty acid methyl ester in coffee beans including a step a) of supplying a methyl group donor to coffee beans and a step c) of roasting the coffee beans after step a) is provided. With this method, a fatty acid methyl ester content of the coffee beans after step c) is preferably increased to 29.5 µg or more per gram of coffee beans. In step a) of supplying a methyl group donor to coffee beans included in the above method, a methyl group donor can be supplied to coffee beans by putting the coffee beans and the methyl group donor in contact with each other. As a means for putting the methyl group donor in contact with the coffee beans, a method such as mixing, spraying, incubating, colliding, and settling can be used. Alternatively, a microorganism that produces a methyl group donor may be grown in the presence of coffee beans. An example of the microorganism that produces a methyl group donor includes methanol-producing bacteria. Timing for supplying the methyl group donor is not limited to particular timing. However, the methyl group donor can be supplied either while green coffee beans are in the process of being carefully selected and dried or while green coffee beans are stored.

The methyl group donor used in the present invention has a methyl group in its molecular structure and is not limited to a particular methyl group donor as long as a methyl group can be provided to other molecules by a substitution reaction, an elimination reaction, or the like. Examples of the methyl group donor typically include methanol, a pectic ingredient, trigonelline, and S-methylmethionine, and a preferable methyl group donor is methanol or pectin. An amount supplied of the methyl group donor is not limited to a particular amount as long as a fatty acid methyl ester content of coffee beans is increased to 29.5 µg or more/g of beans. However, for example, when methanol is used as a methyl group donor, methanol can be supplied so that an amount of a methyl group ($—CH_3$) contained per gram of coffee beans is 0.1 to 200 mg (0.1 to 200 mg/g), preferably 1.0 to 50 mg/g, more preferably 4.5 to 14.0 mg/g.

According to the present invention, the fatty acid methyl ester content of coffee beans after step c) is increased to 29.5 µg/g or more/g of beans, preferably 35.0 µg or more/g of beans, more preferably 40.0 µg or more/g of beans.

A kind of fatty acid methyl ester that is increased by the above method is not limited to a particular kind and is preferably one or more selected from the group consisting of short-chain to long-chain fatty acid methyl esters having a carbon chain of 1 to 28 carbon atoms. The fatty acid methyl ester that is increased by the above method for increasing preferably includes one or more selected from the group consisting of methyl formate, methyl acetate, methyl propionate, methyl butyrate, methyl valerate, methyl isovalerate, methyl caproate, methyl caprylate, methyl caprate, methyl myristate, methyl palmitate, methyl stearate, methyl linoleate, and methyl oleate, and more preferably includes at least one of methyl isovalerate and methyl palmitate.

A content of each of the components including methyl formate, methyl acetate, methyl propionate, methyl butyrate, methyl valerate, methyl isovalerate, methyl caproate, methyl caprylate, methyl caprate, methyl myristate, methyl palmitate, methyl stearate, methyl linoleate, and methyl oleate in the coffee beans after step c) is not limited to a particular content and is preferably 29.5 μg or more/g of beans, more preferably 35.0 μg or more/g of beans, further more preferably 40.0 μg or more/g of beans. A methyl isovalerate content of the coffee beans after step c) is preferably 0.10 μg or more/g of beans, more preferably 0.14 μg or more/g of beans, further more preferably 0.14 μg or more/g of beans, particularly preferably 0.17 μg or more/g of beans, and a methyl palmitate content of the coffee beans after step c) is preferably 28.0 μg or more/g of beans, more preferably 34.0 μg or more/g of beans, further more preferably 38.0 μg or more/g of beans.

With the method of the present invention, various kinds of flavor components in coffee beans other than the above acid methyl esters can be increased. The flavor component increased by the method of the present invention is not limited to a particular component, and for example, components having a methyl group such as furfuryl methyl ether and methyl 2-furancarboxylate are increased. It is assumed that these components are produced by supplying a methyl donor. These components are known to be contained in high-quality beans, and it is considered that an interaction among these components leads to an improvement in taste. Therefore, with the method of the present invention, a flavor surpassing that of high-quality beans can be given to average-quality beans.

The roasting condition is not limited to a particular condition as long as a fatty acid methyl ester content of coffee beans is increased to 0.12 μg or more/g of beans. However, a roasting temperature is preferably 100 to 300° C., more preferably 140 to 280° C., further more preferably 160 to 260° C. Further, a roasting time is preferably 2 to 180 minutes, more preferably 3 to 120 minutes, further more preferably 4 to 100 minutes. The roasting method and the roast level applied in this method is described as in coffee beans above.

The coffee beans used in the above method may be either green coffee beans or roasted coffee beans and are not limited to these in particular.

As an embodiment of the present invention, a method for increasing fatty acid methyl ester in coffee beans including supplying a pectic ingredient as a methyl group donor to coffee beans in step a) and then warm-treating or normal temperature-treating the coffee beans is provided. More specifically, as an embodiment of the present invention, a method for increasing fatty acid methyl ester in coffee beans including a step a) of supplying a pectic ingredient to coffee beans, a step b) of warm-treating or normal temperature-treating the coffee beans after step a), and a step c) of roasting the coffee beans after step b) is also provided. With this method, the fatty acid methyl ester content of the coffee beans after step c) is preferably increased to 29.5 μg or more per gram of coffee beans.

As an embodiment of the present invention, a method for increasing fatty acid methyl ester in coffee beans including a step a) of supplying a methyl group donor to coffee beans is also provided. As an embodiment of the present invention, a step b) of warm-treating or normal temperature-treating the coffee beans after step a) can be further included. Further, as an embodiment of the present invention, a step c) of roasting the coffee beans after step a) or b) can be included. With this method, the fatty acid methyl ester content of the coffee beans is increased to a certain value or more and is preferably increased to 29.5 μg or more per gram of coffee beans.

The pectic ingredient used in the present invention is not limited to a particular ingredient as long as a pectic ingredient can give a methyl group to a fatty acid by a substitution reaction, an elimination reaction, or the like, and such a pectic ingredient preferably includes at least one or more of pectin and a pectin-containing material. As the pectin-containing material, a material containing pulp of a plant can be suitably used. As the pulp of a plant, coffee pulp or grape pulp can be used and a raw material containing grape pulp such as a ground product of grape berries can be used. Therefore, in the method of the present invention, the pulp of a plant preferably includes at least one of coffee pulp and grape berries, and also a freeze-dried product or ground product of the coffee pulp and the grape berries can be suitably used. An amount supplied of the pectic ingredient is not limited to a particular amount as long as a fatty acid methyl ester content of coffee beans is increased to 29.5 μg or more/g of beans.

A warming or normal temperature treatment condition is not limited to a particular condition as long as a fatty acid methyl ester content of coffee beans is increased to 29.5 μg or more/g of beans, and a warming temperature is preferably 20 to 100° C., more preferably 25 to 80° C., further more preferably 40 to 65° C. A warming or normal temperature treatment time is preferably 1 to 96 hours, more preferably 3 to 72 hours, further more preferably 6 to 60 hours. The warming treatment time as used here is an elapsed time from the point in time when the coffee beans are loaded into a warmer if the warmer is prewarmed at a desired temperature and also an elapsed time from the point in time when a temperature of the warmer reaches the desired temperature if the temperature of the warmer is raised after loading the coffee beans into the warmer. As a heating device, an incubator and a desiccator that are capable of controlling a temperature can be used.

As an embodiment of the present invention, an enzyme is supplied in step a) and then an enzyme treatment can be performed in the warming or normal temperature treatment process. This promotes a pectic ingredient to produce a methyl group donor, and thus increases the fatty acid methyl ester content of coffee beans more efficiently. As the enzyme, pectinase or the like is preferably used, pectinase containing at least one of pectin esterase and polygalacturonase is more preferably used, and pectinase containing both pectin esterase and polygalacturonase is further more preferably used. The plural number of enzymes including pectinase and the like can be used in combination.

Timing of supplying an enzyme is not limited to a particular timing as long as a pectic ingredient is present, and supplying of the enzyme can be performed in a carefully selecting step and in the drying step during the process of harvesting coffee fruit to the process of producing green coffee beans, for example. The pectic ingredient may also be supplied after supplying the enzyme.

The coffee beans used in the above method may be either green coffee beans or roasted coffee beans and are not limited to these in particular. A roasting method and a roast level of the coffee beans are as described above.

2-2. A Method for Increasing Fatty Acid Methyl Ester by Carefully Selecting Coffee Fruit As an embodiment of the present invention, a method for increasing fatty acid methyl ester by carefully selecting coffee fruit is provided. More specifically, it is a method for increasing fatty acid methyl ester in coffee beans including a step a) of drying coffee fruit straight after harvesting and a step b) of selecting called a non-washing method in which coffee pulp is removed after step a). The above method may include a step of roasting coffee beans after the carefully selecting step. In the above method, by drying the coffee beans with coffee pulp and coffee pericarp being remained, fatty acid methyl ester in coffee beans can be increased during the above step. Additionally, in the above method, an enzyme can be supplied in the carefully selecting step or before the carefully selecting step. A kind of the enzyme is as described above. With the above method, the fatty acid methyl ester content of coffee beans after step c) is preferably increased to 29.5 µg or more per gram of coffee beans.

On the other hand, in carefully selecting the coffee fruit, a washing method, that is, the method in which removing pulp and pericarp and removing endocarp are separately performed is generally used. More specifically, pulp and pericarp are removed from harvested coffee fruit, and then mucilage (viscous substance) is removed therefrom. A resultant is subjected to a washing and drying step, and endocarp is removed therefrom by threshing to obtain green coffee beans.

In the present invention, a microorganism that produces a methyl group donor is put in contact with coffee beans in the carefully selecting step to produce a methyl group donor. The use of this methyl group donor can increase fatty acid methyl in coffee beans. Further, with the above method, a methyl group donor of a pectic ingredient is treated with an enzyme such as pectinase to produce a methyl group. The use of this methyl group donor can also increase fatty acid methyl ester in coffee beans. Therefore, with the above method, fatty acid methyl in coffee beans can also be increased by using a microorganism that produces a methyl group donor in combination with an enzyme such as pectinase. An embodiment of the step for putting a microorganism in contact with coffee beans is not limited to a particular embodiment.

A kind and an amount of fatty acid methyl ester increased by the above method are as described above. A roasting method and a roast level of coffee beans are also as described above.

Further, with the above method, various flavor components in coffee beans other than the fatty acid methyl esters can be increased. The flavor component increased by the method of the present invention is not limited to a particular component. However, components having a methyl group such as furfuryl methyl ether and methyl 2-furancarboxylate can be increased by the method. It is assumed that these components are produced as the methyl donor increases. These components are also known to be contained in high-quality beans, and it is considered that an interaction among these components leads to an improvement in taste. Therefore, with the method of the present invention, a flavor surpassing that of high-quality beans can be given to average-quality beans.

3. Method for Evaluating Coffee Beans

The plural number of fatty acid methyl esters are known. Those fatty acid methyl esters include the ones having a fruity and fruit-like aroma which are components that strongly contribute to a peculiar flavor of coffee. The present inventors found that a coffee beverage produced by using coffee beans having a fatty acid methyl ester content within a specific range has a good flavor. Therefore, by pre-evaluating an amount of flavor components in coffee beans based on fatty acid methyl ester as an indicator, coffee having a good flavor can be produced easily.

In an aspect of the present invention, a method for evaluating coffee beans having a good flavor including a step of measuring a fatty acid methyl ester content of coffee beans and a step of comparing the fatty acid methyl ester content with a predetermined value is provided. The predetermined value of the fatty acid methyl ester content is preferably 29.5 µg or more per gram of coffee beans, and coffee beans determined to have a fatty acid methyl ester content of 29.5 µg or more per gram of coffee beans can be evaluated as coffee beans having a good flavor. Further, as another embodiment of the present invention, a method for evaluating coffee beans including a step of measuring a fatty acid methyl ester content of coffee beans and a step of determining the coffee beans having a fatty acid methyl ester content of 29.5 µg or more/g of beans is also provided. In this method, coffee beans determined to have a fatty acid methyl ester content of 29.5 µg or more per gram of coffee beans can be evaluated as coffee beans having a good flavor.

The coffee beans used in the evaluation method of the present invention may be either green coffee beans or roasted coffee beans. A species and a production place of the coffee beans used in the method are not limited to a particular species and a particular production place. A kind and a content of fatty acid methyl ester, a species and a production place of coffee beans, a roast level, and the like are described as in coffee beans above.

The fatty acid methyl ester content can be measured by a publicly known method and examples of the method include spectroscopy such as LC-MS method, GC-MS method, LC method, GC method, and a near infrared spectrum.

In the evaluation method of the present invention, coffee beans determined to have a fatty acid methyl ester content of 29.5 µg or more/g of beans, preferably 35.0 µg or more/g of beans, more preferably 40.0 µg or more/g of beans are determined to be suitable for producing a coffee beverage having a good flavor.

In the evaluation method of the present invention, a content of each of the components including methyl formate, methyl acetate, methyl propionate, methyl butyrate, methyl valerate, methyl isovalerate, methyl caproate, methyl caprylate, methyl caprate, methyl myristate, methyl palmitate, methyl stearate, methyl linoleate, and methyl oleate in coffee beans may be used as an indicator. In this case, coffee beans determined to have a methyl isovalerate content of preferably 0.10 µg or more/g of beans, more preferably 0.14 µg or more/g of beans, further more preferably 0.14 µg or more/g of beans, particularly preferably 0.17 µg or more/g of beans, and coffee beans determined to have a methyl palmitate content of preferably 28.0 µg or more/g of beans, more preferably 34.0 µg or more/g of beans, further more preferably 38.0 µg or more/g of beans are determined to be suitable for producing a coffee beverage having a good flavor.

EXAMPLES

Hereinafter, the present invention will be further described in detail with reference to examples. However, the present invention is not limited to these examples.

Example 1: Correlation Between a Fatty Acid Methyl Ester Content of Roasted Coffee Beans and a Flavor Score Fourteen species of Guatemalan green coffee beans were roasted (roast level: L value of 22 to 23) and then a flavor score of a coffee extract was kept in accordance with the protocol of SCAA (Specialty Coffee Associate of America). A sensory evaluation was made by professional panelists. An extract was extracted from 4 g of the ground product obtained by grinding the remaining roasted beans of each species of the coffee beans with 10 mL of a mixed solution of pentane and ether (pentane:ether=1:2) and 100 μL of undecane as an internal standard substance (an acetone solution of 2000 μL/L), at 22 to 24° C. (for 16 hours). The resulting extract was measured by GC-MS. An area value of each signal detected by GC-MS was standardized by an area value of the internal standard, and a correlation between the standardized area value of each signal and the flavor score of the coffee extract was evaluated using multivariate analysis software called SIMCA-P+ (manufactured by Umetrix). A conical burr coffee grinder (manufactured by Delongi) was used to grind the roasted coffee beans. The GC-MS was performed using the following measurement equipment under the following measurement conditions where n=3.

<GC-MS Conditions (for Extraction with a Pentane and Ether Solution, a Liquid Injection Method)>

Device: 7890A (GC) and 5975C (MS) manufactured by Agilent Technologies Inc.

Column: DB-WAXetr (60 m×0.32 mm×0.25 μm) manufactured by GESTEL GmbH & Co. KG

Column temperature: 40° C. (2 min) −4° C./min −250° C. (5 min)

Carrier gas: He

Transfer line: 250° C.

Ion source temperature: 230° C.

Scan Parameter: m/z=33 to 450

Injection volume: 2 μL

Split: None

As a result of the experiment, a correlation was found between the content of fatty acid methyl esters (methyl isovalerate and methyl palmitate) in the roasted beans and the flavor of the coffee extract, and it turned out to be clear that these fatty acid methyl esters serve as a marker that positively correlates with the flavor score of the coffee extract.

Example 2: Correlation Between a Fatty Acid Methyl Ester Content of Roasted Coffee Beans and Flavor Quality An extract was extracted from 4 g of a ground product of two species of Guatemalan roasted coffee beans having a clearly different flavor quality from each other with 10 mL of a mixed solution of pentane and ether (pentane:ether=1:2) and 100 μL of undecane as an internal standard substance (an acetone solution of 2000 μL/L), at 22 to 24° C. (for 16 hours). The resulting extract was measured by GC-MS. An area value of each signal detected by GC-MS was standardized by an area value of the internal standard, and a correlation between the standardized area value of each signal and a flavor score of the coffee extract was evaluated using multivariate analysis software called SIMCA-P+ (manufactured by Umetrix). A conical burr coffee grinder (manufactured by Delongi) was used to grind the roasted coffee beans. The GC-MS was performed using the following measurement equipment under the following conditions where n=3.

<GC-MS Conditions (for Extraction with a Pentane and Ether Solution, a Liquid Injection Method)>

Device: 7890A (GC) and 5975C (MS) manufactured by Agilent Technologies Inc.

Column: DB-WAXetr (60 m×0.32 mm×1.0 μm) manufactured by GESTEL GmbH & Co. KG

Column temperature: 40° C. (2 min) −4° C./min −250° C. (5 min)

Carrier gas: He

Transfer line: 250° C.

Ion source temperature: 230° C.

Scan Parameter: m/z=33 to 450

Injection volume: 2 μL

Split: None

As a result of the experiment, a correlation was found between the content of fatty acid methyl esters (methyl isovalerate and methyl palmitate) in the roasted beans and the flavor of the coffee extract, and it turned out to be clear that these fatty acid methyl esters serve as a marker that positively correlates with the flavor score of the coffee extract.

Example 3: A Method for Increasing Fatty Acid Methyl Ester Using a Fatty Acid Methyl Ester Precursor Example 3-1: A Method for Adding Methanol to Green Coffee Beans Green coffee beans (100 g) sprayed with methanol (1 mL, 2 mL, or 3 mL) and untreated green coffee beans (control) were each roasted. A roast level was adjusted so that the green coffee beans after roasting has an L value of 22 to 23 or 18 to 19. An extract was extracted from 4 g of a ground product obtained by grinding the roasted beans with 10 mL of a mixed solution of pentane and ether (pentane:ether=1:2) and 100 μL of undecane as an internal standard substance (an acetone solution of 2000 μL/L), at 22 to 24° C. (for 16 hours). The resulting extract was measured by GC-MS. An area value of each signal detected by GC-MS was standardized by an area value of the internal standard. A conical burr coffee grinder (manufactured by Delongi) was used to grind the roasted coffee beans. The GC-MS was performed using the following measurement equipment under the following conditions where n=3.

<GC-MS Conditions (for Extraction with a Pentane and Ether Solution, a Liquid Injection Method)>

Device: 7890A (GC) and 5975C (MS) manufactured by Agilent Technologies Inc.

Column: DB-WAXetr (60 m×0.32 mm×0.25 μm) manufactured by GESTEL GmbH & Co. KG

Column temperature: 40° C. (2 min) −4° C./min −250° C. (5 min)

Carrier gas: He

Transfer line: 250° C.

Ion source temperature: 230° C.

Scan Parameter: m/z=33 to 450

Injection volume: 2 μL

Split: None

The results are shown in Table 1 and FIG. 1. In Table 1, methyl isovalerate is shown as "C5'Me" and methyl palmitate is shown as "C16Me".

TABLE 1

Fatty acid methyl ester content of roasted coffee beans prepared by roasting green coffee beans sprayed with methanol

| Sample | | Roast level (L value) | Content of each component in roasted beans | |
|---|---|---|---|---|
| | | | C5'Me (μg/g of beans) | C16Me (μg/g of beans) |
| [Untreated] | Beans prepared by roasting control green beans (untreated) | L22-23 | 0.053 | 13.04 |
| [+Methanol (1 mL)] | Beans prepared by roasting 100 g of green beans sprayed with 1 mL of methanol | L22-23 | 0.364 | 39.66 |
| [+Methanol (2 mL)] | Beans prepared by roasting 100 g of green beans sprayed with 2 mL of methanol | L22-23 | 0.497 | 92.94 |
| [+Methanol (3 mL)] | Beans prepared by roasting 100 g of green beans sprayed with 3 mL of methanol | L22-23 | 0.878 | 145.60 |
| [Untreated] | Beans prepared by roasting control green beans (untreated) | L18-19 | 0.072 | 17.68 |
| [+Methanol (1 mL)] | Beans prepared by roasting 100 g of green beans sprayed with 1 mL of methanol | L18-19 | 0.371 | 40.41 |
| [+Methanol (2 mL)] | Beans prepared by roasting 100 g of green beans sprayed with 2 mL of methanol | L18-19 | 0.423 | 79.04 |
| [+Methanol (3 mL)] | Beans prepared by roasting 100 g of green beans sprayed with 3 mL of methanol | L18-19 | 0.723 | 119.99 |

As shown in Table 1 and FIG. 1, as a result of roasting green coffee beans sprayed with methanol, the content of fatty acid methyl esters (methyl isovalerate and methyl palmitate) in roasted coffee beans was increased according to an amount of methanol sprayed when comparing the above-mentioned roasted coffee beans with the control roasted beans.

Example 3-2: A Method for Treating Green Coffee Beans by Adding Pectinase or Water to a Ground Product of Coffee Pulp and Pericarp To 17 g of a ground product of pulp and pericarp extracted from coffee fruit, 1 mL of pectinase PL "Amano" (Amano Enzyme Inc.) which is an enzyme for food industries/24 mL or 25 mL of water was added to produce a slurry. 50 g of green coffee beans was added to the slurry, which was incubated at 45° C. for 48 hours. As a control sample, untreated green beans, green beans in 25 mL of water (room temperature), and beans incubated in 25 mL of water at 45° C. were prepared. The resulting treated beans and control beans were partially frozen and then ground to analyze an amount of methanol contained by headspace (HS)-GC-MS. Further, a water content was measured, and an area value obtained by HS-GC-MS was converted to a calculated value per weight of dried green beans based on the water content. The remaining treated beans and control beans were roasted and subjected to GC-MS measurement in the same manner as in Example 3-1. The HS-GC-MS was performed using the following measurement equipment under the following conditions where n=3.
<HS-GC-Ms Conditions>
Device: 7890A (GC) and 5975C (MS) manufactured by Agilent Technologies Inc. and MPS manufactured by GERSTEL GmbH & Co. KG
Column: DB-WAXetr (60 m×0.32 mm×1.0 μm) manufactured by GESTEL GmbH & Co. KG
Column temperature: 50° C. (20 min) –10° C./min –150° C. –40° C./min (2 min)
Carrier gas: He
Transfer line: 250° C.
Ion source temperature: 230° C.
Scan Parameter: m/z=29 to 300
HS gas injection volume: 200 μL
Split ratio: 5:1

The results are shown in Table 2, Table 3, and FIG. 2. In Table 3, methyl isovalerate is shown as "C5'Me" and methyl palmitate is shown as "C16Me".

TABLE 2

| | Sample | Methanol content (value calculated from the HS-GC-MS area value based on the water content) |
|---|---|---|
| [Control 1] | Control green beans (untreated) | 639 |
| [Control 2] | Green beans treated in 25 mL of water | 820 |
| [Control 3] | Green beans incubated in 25 mL of water at 45° C. for 48 hours | 424 |
| [Test 1] | Green beans incubated at 45° C. for 48 hours under conditions of addition of coffee pulp and pericarp, 1 mL of pectinase PL, and 24 mL of water | 9700 |
| [Test 2] | Green beans incubated at 45° C. for 48 hours under conditions of addition of coffee pulp and pericarp and 25 mL of water | 11516 |

TABLE 3

Fatty acid methyl ester content of roasted coffee beans prepared by roasting green coffee beans treated under various conditions

| Sample | | Roast level (L value) | C5'Me (μg/g of beans) | C16Me (μg/g of beans) |
|---|---|---|---|---|
| [Control 1] | Beans prepared by roasting control green beans (untreated) | 19.7 | 0.093 | 26.81 |
| [Control 2] | Beans prepared by roasting green beans treated in 25 mL of water | 19.2 | 0.076 | 26.18 |
| [Control 3] | Beans prepared by roasting green beans incubated in 25 mL of water at 45° C. for 48 hours | 19.2 | 0.061 | 27.70 |
| [Test 1] | Beans prepared by roasting green beans incubated at 45° C. for 48 hours under conditions of addition of coffee pulp and pericarp, 1 mL of pectinase PL, and 24 mL of water | 16.6 | 0.171 | 91.36 |
| [Test 2] | Beans prepared by roasting green beans incubated at 45° C. for 48 hours under conditions of addition of coffee pulp and pericarp and 25 mL of water | 16.9 | 0.244 | 100.84 |

As shown in Table 2, as a result of treating the green coffee beans with coffee pulp and pericarp, the methanol content of the green coffee beans was increased. Table 3 and FIG. 2 clearly show that methyl isovalerate and methyl palmitate were richly contained in the roasted coffee beans prepared by roasting green coffee beans treated with coffee pulp and pericarp, and in addition to that, the content of those components was further increased by treating green coffee beans with coffee pulp and pericarp and pectinase PL.

Example 3-3: A Method for Treating Green Coffee Beans by Adding Pectinase or Water to a Ground Product of Grape Berries A test was conducted using grape berries as a material containing pulp of a plant. To a slurry made of a mixture of a ground product (50 g) of the grape berries and pectinase PL "Amano" (Pec PL: Amano Enzyme Inc.), pectinase G "Amano" (Pec G: Amano Enzyme Inc.), or pectinase MP (Pec MP: MP Biomedicals), 50 g of green coffee beans was added, which was incubated at 45° C. for 48 hours. As a control, untreated green beans, green coffee beans in 25 mL of water (room temperature), and green coffee beans incubated in 25 mL of water at 45° C. were prepared. A methanol content of the treated beans and the untreated beans was measured by HS-GC-MS in the same manner as in Example 3-2, and a calculated value per weight of dried green beans was determined from the measured content based on the water content.

The results are shown in Table 4 and FIG. 3.

TABLE 4

| Sample | | Methanol content (value calculated from the HS-GC-MS area value based on the water content) |
|---|---|---|
| [Control 1] | Control green beans (untreated) | 639 |
| [Control 2] | Green beans treated in 25 mL of water | 820 |
| [Control 3] | Green beans incubated in 25 mL of water at 45° C. for 48 hours | 424 |
| [Test 1] | Green beans incubated at 45° C. for 48 hours under conditions of addition of a ground product of grape berries, 1 mL of pectinase PL, and 24 mL of water | 1623 |
| [Test 2] | Green beans incubated at 45° C. for 48 hours under conditions of addition of a ground product of grape berries, 1 mL of pectinase G, and 24 mL of water | 2022 |
| [Test 3] | Green beans incubated at 45° C. for 48 hours under conditions of addition of a ground product of grape berries, 1 mL of pectinase MP, and 24 mL of water | 1478 |

As shown in Table 4 and FIG. 3, as a result of treating green coffee beans with the ground product of grape berries, the methanol content of the green coffee beans was increased. Further, Table 4 and FIG. 3 clearly show that as a result of treating green coffee beans with the ground product of grape berries and pectinase, the methanol content of the green coffee beans was further increased. This suggests that methyl isovalerate and methyl palmitate were richly contained in roasted coffee beans subjected to the above-mentioned treatment.

Example 3-4: A Method for Increasing Fatty Acid Methyl Ester by Treating Green Coffee Beans by Adding Pectinase to Pectin To pectin (40 g) (UNIPEKTIN Ingredients AG, derived from an apple), pectinase FE/water (100 mL) was added and then Guatemalan average-quality green coffee beans (100 g) was added, which was incubated at 45° C. for 48 hours. The resulting treated beans were roasted and subjected to the GC-MS measurement in the same manner as in Example 3-1 to calculate a proportion of an amount of methyl palmitate produced in the treated beans as an amount relative to a methyl palmitate content of the average-quality green coffee beans. Additionally, an amount of methyl palmitate in high-quality roasted coffee beans were measured as a comparison case.

The results are shown in Table 5.

TABLE 5

Ratio of the amount of methyl palmitate produced in roasted coffee beans

| | Ratio of the amount of methyl palmitate produced (amount relative to the methyl palmitate content of average-quality roasted beans) |
|---|---|
| Average-quality roasted beans | 1 |
| Roasted beans prepared by treating average-quality green coffee beans with pectin and pectinase | 2.5 |
| High-quality roasted beans | 4.2 |

As shown in Table 5, as a result of treating Guatemalan average-quality green coffee beans with pectin and roasting thereafter, the methyl palmitate content of the roasted coffee beans was increased.

Example 4: A Sensory Evaluation of Coffee Beverage Having Increased Fatty Acid Methyl Ester

Example 4-1: A Sensory Evaluation of Coffee Beverage Containing Methyl Isovalerate After adding fatty acid methyl ester to a coffee beverage, a change in flavor characteristics caused by the addition of fatty acid methyl ester was evaluated. 30 g of roasted coffee powder obtained by roasting average-quality green coffee beans (L value of 18 to 19) was subjected to extraction with $H_2O$ (300 mL) at 97° C., and the resulting extract was diluted with $H_2O$ to produce a base coffee beverage so that the base coffee beverage had Brix of 1.0. To this coffee beverage, methyl isovalerate as an aromatic were added so that the final concentration thereof in the coffee beverage was 25 ppb or 50 ppb, which was subjected to a sensory evaluation by 6 panelists. As a result, the panelists commented that the coffee beverage had increased acidity and reduced acridity and thus gave a mild impression to the panelists at either concentration. Therefore, it is confirmed that the flavor characteristics were improved by the addition of methyl isovalerate.

Example 4-2: A Sensory Evaluation of a Packaged Coffee Beverage Containing Methyl Isovalerate To determine whether an increase in a methyl isovalerate content has an effect on an improvement in flavor characteristics, a sensory evaluation was made as follows. Each panelist was provided with packaged beverages each marked with a sign for identification that has nothing to do with contents without giving any information on details of the beverages.

<Beverage Used for the Sensory Evaluation>

The following three kinds of coffee beverages were used.

Coffee beverage 1: A beverage produced by using roasted coffee beans of the same quality as the roasted coffee beans used for a commercially available canned coffee Coffee beverage 2: A beverage produced by adding methyl isovalerate to Coffee beverage 1

Coffee beverage 3: A beverage produced by using high-quality roasted coffee beans All the above coffee beverages were extracted from roasted beans roasted to a medium degree using the same extraction method. After the extraction, Coffee beverages 1 and 3 were adjusted so that their Brix values were equal to each other. Further, to Coffee beverage 2, methyl isovalerate was added so that a final concentration thereof in the beverage was 50 ppb. After that, Coffee beverages 1 to 3 were packaged and sterilized with heat, and the sensory evaluation was made thereafter.

(1) Sensory Evaluation 1: A Sensory Evaluation by Ordinary Panelists

Panelist for the Sensory Evaluation:

42 working males at their twenties to forties who often drink commercially available coffee beverages <Sensory Evaluation 1-1>

To determine whether there is a difference in flavors between Coffee beverages 1 and 3, a discrimination test was conducted by a triangle discrimination method. As a result, both beverages were significantly distinguishable (discrimination rate 50%/significance level 10%/significance probability 2%), and it is confirmed that there was a difference in the flavors between Coffee beverages 1 and 3.

<Sensory Evaluation 1-2>

When the ordinary panelists were questioned about an element that they felt a difference in the above Sensory evaluation 1-1, many panelists pointed out the difference in an intensity of bitterness or acidity as shown in FIG. 4. Accordingly, the bitterness and acidity intensity of both beverages were compared with each other by a paired comparison method. As a result, a large number of panelists pointed out that Coffee beverage 1 had a stronger bitterness, and in contrast, a large number of panelists pointed out that Coffee beverage 3 had a stronger acidity. Based on the above, a main difference of the flavors between Coffee beverages 1 and 3 was the intensity of bitterness and acidity, and thus it was considered that weakening bitterness and intensifying acidity would improve the flavor quality of Coffee beverage 1.

(2) Sensory Evaluation 2: A Sensory Evaluation by Professional Panelists

Panelist for the Sensory Evaluation:

6 employed professional panelists who are experienced in the sensory evaluation of a coffee beverage <Sensory Evaluation>

The above Sensory evaluation 1 suggests that a difference in the flavor quality of Coffee beverages 1 and 3 was caused by the intensity of acidity and bitterness. Therefore, a sensory evaluation was made by professional panelists to determine how the addition of methyl isovalerate affects acidity and bitterness of a coffee beverage. Coffee beverages 1 to 3 were paired with each other to provide three combinations in total, and an evaluation was made by a paired comparison method. As a result, as suggested in Sensory evaluation 1-2, Coffee beverage 1 had significantly stronger bitterness and Coffee 3 had significantly stronger acidity. On the other hand, Coffee beverage 2 produced by adding methyl isovalerate to Coffee beverage 1 had bitterness and acidity close to those of Coffee beverage 3, and thus it turned out to be clear that Coffee beverages 1 and 3 were indistinguishable from each other.

(3) Sensory Evaluation 3: Evaluation (2) Made by Ordinary Panelists

Panelist for the Sensory Evaluation:

42 working males at their twenties to forties who often drink commercially available coffee beverages <Sensory Evaluation>

The above Sensory evaluation 2 suggests that by adding methyl isovalerate to Coffee beverage 1, the bitterness and acidity causing a difference in the flavor quality of Coffee beverages 1 and 3 come close to those of Coffee beverage 3. Given this situation, a discrimination test was conducted on Coffee beverages 2 and 3 by a triangle discrimination method. As a result, both beverages were indistinguishable (discrimination rate 43%/significance level 10%/significance probability 13%), and thus this proves that methyl isovalerate was effective in improving the flavor quality of a coffee beverage.

Example 4-3: A Sensory Evaluation of Beans Having a Fatty Acid Methyl Ester Content Increased by Using a Pectic Ingredient 30 g of the roasted coffee beans having an increased fatty acid methyl ester content prepared by roasting Guatemalan average-quality green coffee beans treated with pectin and pectinase FE prepared in the above Example 3-4, 30 g of Guatemalan average-quality roasted beans (control), and 30 g of Guatemalan high-quality roasted beans (positive control) were each ground and then filtered by 300 mL of hot water to produce coffee beverages. A sensory evaluation test was conducted on the resulting coffee beverages by 4 panelists who are experienced in a sensory evaluation. Acidity, bitterness, and acridity of each coffee beverage were rated on a scale of 1 to 5 by each panelist, and an average value was regarded as a sensory score of acidity, bitterness, or acridity.

The results are shown in Table 6.

TABLE 6

|  | Acidity | Acridity | Bitterness |
|---|---|---|---|
| Coffee beverage derived from average-quality roasted beans | 3 | 3 | 4 |
| Coffee beverage derived from roasted beans prepared by treating average-quality green coffee beans with pectin and pectinase | 3.5 | 2.5 | 3 |
| Coffee beverage derived from high-quality roasted beans | 4 | 1 | 2.5 |

As shown in Table 6, the coffee beverage prepared by using roasted coffee beans having a fatty acid methyl ester content increased by treating average-quality green coffee beans with pectin and pectinase had a high acidity score and low acridity and bitterness scores as compared with a coffee beverage derived from control beans, and thus, the flavor of the coffee beverage came close to that of a coffee beverage derived from high-quality roasted coffee beans. Therefore, the flavor quality was improved in the coffee beverage produced from the roasted beans having methyl ester increased by using pectin and pectinase (Table 5).

Example 4-4: A Sensory Evaluation of Beans Having a Fatty Acid Methyl Ester Content Increased by Adding Methanol A sensory evaluation was made in regard to two standard of roasted beans (L22 to 23) each having a fatty acid methyl ester content increased by adding methanol prepared in the above Example 3-1 (the roasted beans each prepared by roasting 100 g of green beans after adding 1 mL or 2 mL of methanol to the green beans), in the same manner as in Example 4-3. The sensory evaluation was made by 6 professional panelists using untreated roasted beans as a control for a comparative example.

As a result of the study, it shows that beans having a fatty acid methyl ester content increased by spraying methanol had stronger acidity, a stronger fruity aroma, and less acridity than those of the control, and thus had a clean finish. These characteristics are sensory axes common to beans having high flavor quality.

Example 5: Fixed Quantity of Fatty Acid Methyl Ester in a Coffee Beverage

Roasted beans prepared by roasting Guatemalan average-quality beans (control green beans), roasted beans prepared by roasting 100 g of control green beans sprayed with 2 mL of methanol, and roasted beans prepared by roasting Guatemalan high-quality beans were each ground (10 g). 100 mL of water at 97° C. was poured to each ground product to extract coffee for 5 minutes, and coffee beverages were produced accordingly. After that, the prepared coffee beverages were each filtered and 20 mL of each filtered coffee beverage was adsorbed onto PoraPak™ Q resin (50 to 80 mesh, manufactured by GL Sciences Inc.) (150 mg), which was eluted out with 1 mL of dichloromethane. Benzoisocyanate was used as an internal standard substance. GC-MS analysis was performed by a liquid injection method in the same manner as in Example 3-1.

The results are shown in Table 7. In Table 7, methyl isovalerate is shown as "C5'Me".

TABLE 7

|  | C5'Me content of coffee beverage (ppb) |
|---|---|
| Coffee beverage derived from high-quality beans | 22.0 |
| Coffee beverage derived from average-quality beans | 11.4 |
| Coffee beverage derived from beans prepared by roasting average-quality beans sprayed with methanol | 104.3 |

As shown in Table 7, the methyl isovalerate-rich coffee beverage was produced by preparing a coffee beverage using the roasted beans having a fatty acid methyl ester content increased by spraying methanol on average-quality green coffee beans.

Example 6: Evaluation of Various Components in Coffee Beans Increased by a Method for Increasing Fatty Acid Methyl Ester With the method of the present invention, various flavor components having a methyl group other than fatty acid methyl ester are increased. Accordingly, a study of the other flavor components having a methyl group was conducted on the roasted coffee beans having fatty acid methyl ester increased by spraying methanol on green coffee beans as shown in Table 1 of Example 3-1. More specifically, an increased amount of furfuryl methyl ether and methyl 2-furancarboxylate in addition to methyl isovalerate in roasted coffee beans was evaluated. Analyzing conditions were set in accordance with the GC-MS method as described in Example 3-1.

The results are shown in Table 8.

TABLE 8

| | | | | Content of each component in roasted beans | |
|---|---|---|---|---|---|
| | Sample | Roast level (L value) | C5'Me (μg/g of beans) | Furfuryl methyl ether (GCMS area value [ratio to IS]) | Methyl 2-furancarboxylate (GCMS area value [ratio to IS]) |
| Beans prepared by roasting average-quality green beans | Beans prepared by roasting control green beans | 22-23 | 1.0 | 1.0 | 1.0 |
| | Beans prepared by roasting control green beans | 18-19 | 1.4 | 1.7 | 1.8 |
| Beans prepared by roasting average-quality green beans processed | Beans prepared by roasting 100 g of green beans sprayed with 1 mL of methanol | 22-23 | 6.9 | 7.8 | 11.6 |
| | Beans prepared by roasting 100 g of green beans sprayed with 2 mL of methanol | 22-23 | 9.4 | 13.2 | 19.5 |
| | Beans prepared by roasting 100 g of green beans sprayed with 3 mL of methanol | 22-23 | 16.6 | 24.5 | 27.2 |
| | Beans prepared by roasting 100 g of green beans sprayed with 1 mL of methanol | 18-19 | 7.0 | 7.0 | 6.5 |
| | Beans prepared by roasting 100 g of green beans sprayed with 2 mL of methanol | 18-19 | 8.0 | 10.3 | 10.4 |
| | Beans prepared by roasting 100 g of green beans sprayed with 3 mL of methanol | 18-19 | 13.6 | 20.1 | 22.2 |
| Beans prepared by roasting high-quality green beans | High-quality roasted beans A | 23 | 1.8 | 1.1 | 1.5 |
| | High-quality roasted beans B | 18-19 | 1.6 | 1.1 | 1.0 |

Table 8 clearly shows that flavor components having a methyl group such as furfuryl methyl ether and methyl 2-furancarboxylate other than methyl isovalerate as fatty acid methyl ester were increased in the roasted coffee beans having fatty acid methyl ester increased by spraying methanol on green coffee beans. It is assumed that these components were produced by supplying a methyl donor, and further, an amount of the flavor components after the above treatment was more than that of high-quality beans. For that reason, it is considered that in addition to fatty acid methyl ester, these components also contribute to an improvement in a suitable flavor of coffee beans. Therefore, it is suggested that with the method of the present invention, a flavor surpassing that of high-quality beans can be given to average-quality beans.

INDUSTRIAL APPLICABILITY

The present invention provides coffee beans having a fatty acid methyl ester content of a specific value or more, a method for increasing fatty acid methyl ester in coffee beans, and a method for evaluating coffee beans. The present invention relates to a new way of providing coffee beans having an increased content of fatty acid methyl ester that strongly contributes to a flavor of coffee, and thus has high industrial applicability.

The invention claimed is:

1. A coffee bean comprising methyl isovalerate and methyl palmitate as fatty acid methyl esters,
    wherein the coffee bean has (i) a fatty acid methyl ester content of 29.5 μg or more per gram of the coffee bean; (ii) a methyl isovalerate content of 0.10 μg or more per gram of the coffee bean; and (iii) a methyl palmitate content of 28.0 μg or more per gram of the coffee bean.

2. The coffee bean according to claim 1, wherein the coffee bean is a roasted coffee bean.

3. The coffee bean according to claim 1, having an L value of 14 or more.

4. A coffee beverage prepared by using the coffee bean according to claim 1.

5. The coffee beverage of claim 4, having a methyl isovalerate content of 25 ppb or more.

6. A method for increasing a fatty acid methyl ester content of a coffee bean, comprising the steps of:
    a) supplying a methyl group donor to a coffee bean;
    b) warm-treating the methyl group donor supplied coffee bean; and
    c) roasting the warm-treated coffee bean to obtain a roasted coffee bean,
    wherein the roasted coffee bean comprises methyl isovalerate and methyl palmitate as fatty acid methyl esters, and
    wherein the roasted coffee bean has (i) a fatty acid methyl ester content of 29.5 μg or more per gram of the roasted coffee bean; (ii) a methyl isovalerate content of 0.10 μg or more per gram of the roasted coffee bean; and (iii) a methyl palmitate content of 28.0 μg or more per gram of the roasted coffee bean.

7. The method according to claim 6, wherein the methyl group donor comprises at least one or more selected from the group consisting of methanol, a pectic ingredient, trigonelline, and S-methylmethionine.

8. The method according to claim 7, wherein the pectic ingredient comprises at least one or more of pectin and a pectin-containing material.

9. The method according to claim 8, wherein the pectin-containing material comprises pulp of a plant.

10. The method according to claim 9, wherein the pulp of a plant comprises at least one of coffee pulp and a grape berry.

11. The method according to claim 6, further comprising a step of supplying pectinase to the coffee bean in step a).

12. A method for evaluating a coffee bean, comprising:
    a step of measuring a fatty acid methyl ester content of the coffee bean; and
    a step of comparing the fatty acid methyl ester content with a predetermined value to evaluate a flavor of the coffee bean,
    wherein the following values correspond to an improved flavor: (i) a fatty acid methyl ester content of 29.5 μg or more per gram of the coffee bean; (ii) a methyl isovalerate content of 0.10 μg or more per gram of the coffee bean; and (iii) a methyl palmitate content of 28.0 μg or more per gram of the coffee bean.

* * * * *